US00PP20126P3

(12) United States Plant Patent
Maness

(10) Patent No.: US PP20,126 P3
(45) Date of Patent: Jun. 23, 2009

(54) ***ATHYRIUM* PLANT NAMED 'OCEAN'S FURY'**

(50) Latin Name: ***Athyrium* spp.**
Varietal Denomination: Ocean's Fury

(76) Inventor: Thurman Maness, 5233 US Hwy. 64 West, Pittsboro, NC (US) 27312

( * ) Notice: Subject to any disclaimer, the term of this patent is extended or adjusted under 35 U.S.C. 154(b) by 2 days.

(21) Appl. No.: 11/980,128

(22) Filed: Oct. 29, 2007

(65) Prior Publication Data

US 2009/0113588 P1 Apr. 30, 2009

(51) Int. Cl.
*A01H 9/00* (2006.01)

(52) U.S. Cl. ..... Plt./379

(58) Field of Classification Search ..... Plt./379
See application file for complete search history.

(56) References Cited

PUBLICATIONS

Eberly Public Relations, Athyrium 'Ocean's Fury 'Terra Nova Nurseries, Date Unknown, Available at: http://www-.terranovanurseries.com/wholesale/press_release/Athyrium-–Oceans–Fury.pdf.*

* cited by examiner

*Primary Examiner*—Susan B McCormick Ewoldt
(74) *Attorney, Agent, or Firm*—Klarquist Sparkman, LLP

(57) ABSTRACT

A new and distinct cultivar of *Athyrium* characterized in having a strongly upright habit, and leaves of a pewter tone, silver over grey green, with crested tips, and a reddish rachis. This coloring persists from new growth to mature leaves.

1 Drawing Sheet

Botanical Classification: *Athyrium* spp.
Variety Denomination: 'Ocean's Fury'.
Parentage: *Athyrium niponicum* var. pictum and *Athyrium filix-femina* 'Congestum Cristatum' (unpatented).

BACKGROUND OF THE INVENTION

The present invention relates to a new and distinct *Athyrium* and given the cultivar name of 'Ocean's Fury'. *Athyrium* is in the family Woodsiaceae. This new cultivar originated from a cross between *Athyrium niponicum* var. pictum and *Athyrium filix-femina* 'Congestum Cristatum'. This new cultivar is a single selection from the cross.

The new variety has been reproduced only by asexual propagation (tissue culture). Each of the clones exhibits identical characteristics to the original selection.

SUMMARY OF THE INVENTION

This plant is unique in having:

1. A strongly upright habit, and leaves of a pewter tone; and
2. Silver over grey green, with crested tips, and a reddish rachis. This coloring persists from new growth to mature leaves.

Asexual propagation by tissue culture from crown culture as done in Canby, Oreg., shows that the foregoing characteristics and distinctions come true to type and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a three-year-old *Athyrium* 'Ocean's Fury' growing in the ground in a shaded site in Canby, Oreg.

DETAILED PLANT DESCRIPTION

The following is a detailed description of the new *Athyrium* based on observations of four-year-old specimens grown in the ground in a shade structure in Canby, Oreg. The color descriptions are all based on The Royal Horticultural Society Colour Chart, from an edition purchased in 2000.

Plant:
- *Form.*—Terrestrial, clumping.
- *Hardiness.*—USDA Zones 5 to 8.
- *Size.*—80 cm wide and 85 cm tall.

Foliage:
- *Type.*—Compound.
- *Shape.*—Lanceolate to elliptic overall, twice pinnate, pinnae lanceolate with a crested tip, pinnules lanceolate to linear with a crested tip, pinnules pinnatifid.
- *Size.*—Grows to 85 cm long and 27 cm wide, pinnae grow to 19 cm long and 4 cm wide, pinnules grow to 2 cm long and 3 mm wide.
- *Margins.*—Pinnules pinaatifid.
- *Apex.*—Crested at apex of pinnae with main vein splitting into two twice and branching out and pinnules to a lesser degree.
- *Surface texture.*—Glabrous on both sides.
- *Leaf color.*—Topside: pinnule centers Yellow Green 148C, sides Yellow Green 147B, and tips Yellow Green 147A. Bottom side: crests Yellow Green 147A, sori Brown 200D.
- *Rachis color.*—Greyed Red 182A on top side and Yellow Green 152B on back side.
- *Petiole description.*—Grows to 20 cm long and 5 mm wide, glabrous with chaffy scales (Greyed Orange 175A), heaviest at the base, Brown 200C on side closest to plant center and Yellow Green 152B on back side.

Fruiting body:

*Type.*—Sporangium.

*Fertility.*—Very low.

*Sori.*—In clusters on ultimate pinnules, indusium on side closest to the margin. Size — 1 to 2 mm at the widest. Immature — Brown 200D. Sporulating — Brown 200D.

Diseases and Pests: Some *Athyrium* are prone to rust. No diseases have been observed on plants grown commercially in Canby, Oreg. *Athyrium* generally have no pest problems.

Comparisons:

The instant plant resulted from a cross between *Athyrium niponicum* var. pictum and *Athyrium filix-femina*. 'Congestum Cristatum' (unpatented). Compared to *Athyrium niponicum* var. pictum, *Athyrium* 'Ocean's Fury' has very different foliage shape. It does show the coloration of the Japanese Painted Fern with the red in the stipe and the grey green tones in the leaves.

Compared to its other parent *Athyrium filix-femina* 'Congestum Cristatum', the new variety has different leaf shape and coloring but does show the cresting.

There are no other *Athyrium* plants known to the inventor. This new cultivar is unique in its combination of habit and coloration.

I claim:

1. A new and distinct *Athyrium* plant substantially as shown and described.

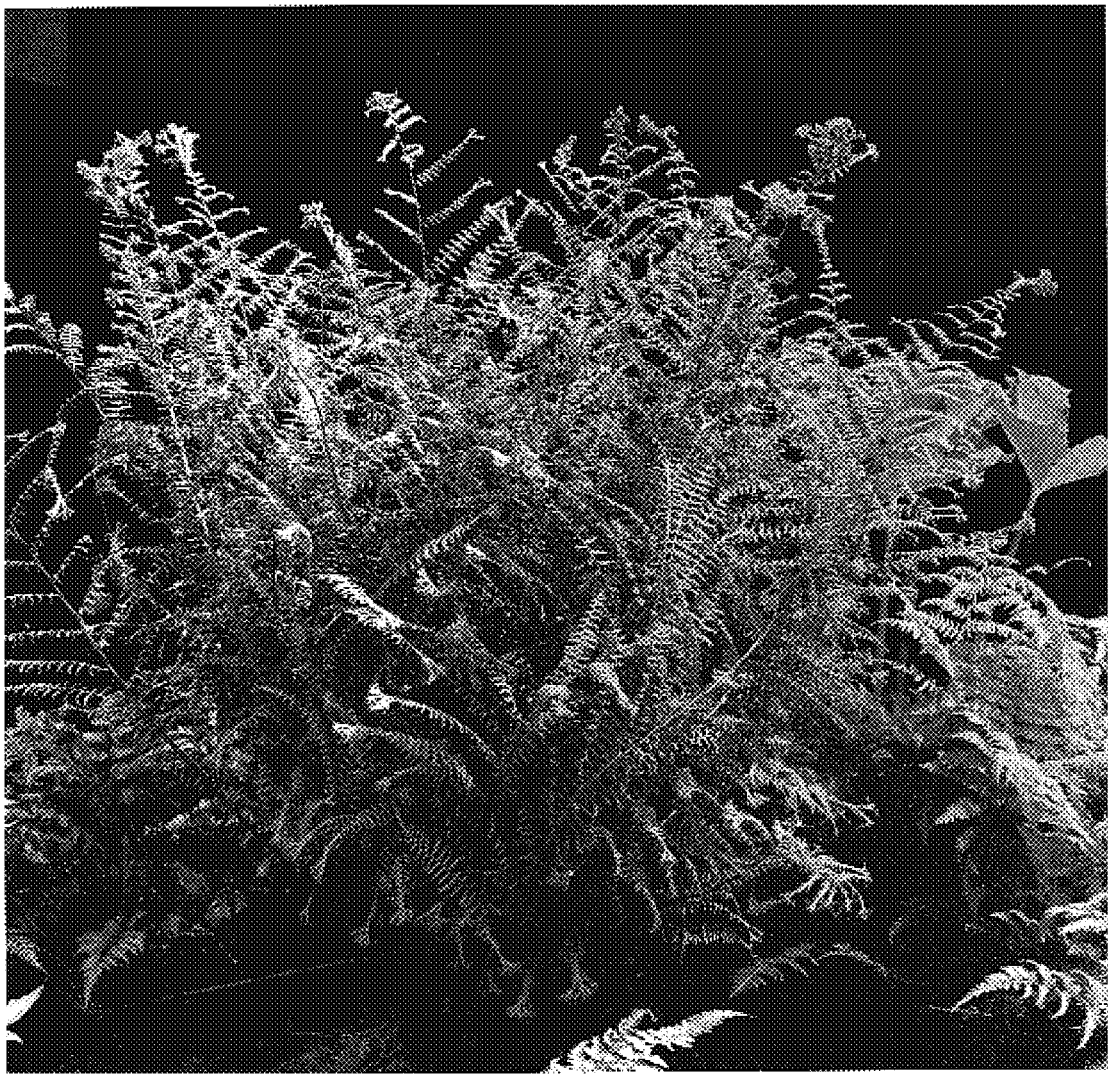

* * * * *